United States Patent [19]

Mayer

[11] 4,360,015
[45] Nov. 23, 1982

[54] MULTILAYER ABSORBENT STRUCTURE
[75] Inventor: Nathan Mayer, East Brunswick, N.J.
[73] Assignee: Hartford Corporation, New Brunswick, N.J.
[21] Appl. No.: 263,685
[22] Filed: May 14, 1981
[51] Int. Cl.³ ............................................. A61L 15/00
[52] U.S. Cl. .................................... 128/156; 128/296
[58] Field of Search ................... 128/284, 287, 290 R, 128/296, 156, 155

[56] References Cited
U.S. PATENT DOCUMENTS

| | | | |
|---|---|---|---|
| 3,122,141 | 2/1964 | Crowe | 128/296 |
| 3,156,242 | 11/1964 | Crowe | 128/296 |
| 3,301,257 | 1/1967 | Crowe et al. | 128/296 |
| 3,683,921 | 8/1972 | Brooks et al. | 128/156 |
| 3,886,941 | 6/1975 | Duane et al. | 128/156 |
| 3,888,248 | 6/1975 | Moore et al. | 128/156 |
| 3,908,645 | 9/1975 | Sandvig | 128/97 |
| 3,965,906 | 6/1976 | Karami | 128/156 |

Primary Examiner—C. Fred Rosenbaum
Attorney, Agent, or Firm—Gary M. Nath

[57] ABSTRACT

A multilayer absorbent bandage and process for making the same having two absorbent layers separated by a grid material and covered on one side by an exterior layer which contacts the wound surface and on the other side by a moisture resistant barrier. The bandage is designed to maintain its structural integrity while being capable of absorbing large amounts of fluid.

16 Claims, 2 Drawing Figures

MULTILAYER ABSORBENT STRUCTURE

DESCRIPTION OF THE INVENTION

This invention relates to an absorbent pad or dressing for use on wounds, surface lesions or burns, and particularly, for use as a bandage for wrapping around a burn wound.

Many different kinds of absorbent bandages are known. These bandages have generally been applied to any part of the trunk or limbs of the body by either being taped to cover the wound or incision or simply rest on the injury with the patient in a reclining position. While such bandages have been quite satisfactory for fresh wounds or immediately following surgery, they have not been completely satisfactory in the case of a burn wound where a large amount of fluid exudes from the wound or burn. In such cases, it is important that the pad or bandage have a high capacity for absorbing and transmitting fluid in order to furnish a substantial supply of water to the burn victim to primarily offset dehydration, a major cause of burn deaths.

One approach at preparing a multilayer bandage for burn wounds was developed during World War II which comprised the use of a thick pad in which the outer surface was made of a non-woven porous craft paper, coarse wax impregnated covering an internal structure comprising many layers of absorbent tissue with an innermost layer of gauze. Upon wetting and use, the inner absorbent tissue tended to clump and bag at the lower end of the burn pad. As the wetting action increased to offset dehydration, the pad's usefulness continued to decline. In addition, such pads did not permit use of effective burn treatment medication without continuous and and rapid removal of the burn pad, which when opened tended to remove burned tissue while injuring less damaged tissue. Bandages designed like the World War II pads have been continually used with the same disadvantages. In the absence of a burn pad, linens, toweling and the like have often been applied to burn victims with detrimental consequences.

A bandage has been unexpectedly discovered which does not have the aforementioned disadvantages. In one aspect of this invention, there is provided a multilayer bandage which comprises: (1) an exterior layer which contacts the wound surface; (2) an absorbent cellulosic layer joined to the first exterior layer; (3) a nonabsorbent grid material which is joined on one side to the cellulosic layer and on the other side to a flexible absorbent member; (4) said flexible absorbent member being formed of a flexible sheet of sponge material containing a web of absorbent fibers disposed on said flexble sheet and extending into the flexible sheet without extending through the flexible sheet; and (5) a moisture resistant barrier layer joined to the sponge material portion of the flexible absorbent member making an outer layer.

When the bandage of the invention is formed in this manner, the bandage construction is capable of holding a substantial amount of fluid to offset dehydration while enabling the use of burn treatment medication, such as silver iodide, in the absorbed liquid. As a result, effective concentrations of the burn treatment medication may be maintained in the bandage for contact on the burn wounds without requiring constant change as required with conventional systems.

An important feature of the invention involves the use of a grid material to bind the weakly bonded absorbent cellulosic material to the main absorbent member. This arrangement enables the rapid lateral spread of fluid in the bandage within the cellulosic material to the flexible absorbent member which acts to rapidly absorb fluid from the cellulosic material in a vertical direction. This unique feature is essential for uniting the two main absorbent layers in a manner which does not interfere with the flow of fluid between them and yet creates a bandage which is highly resistant to tearing in all directions. The direct attachment of the two absorbent layers in the absence of the grid material would form an unacceptable absorbent pad which is unable to hold and transfer sufficient fluid to adequately aid the wounds of the burn victims. As a result of this unique arrangement, a large capacity of water can be retained in the pad. Fluids from the wound are able to drain into the pad and be replaced by water which may optionally contain soothing and therapeutic medications to assist in the healing process. Thus, the amount of water that a given pad will hold and retain while maintaining its structural integrity is quite critical.

The bandage of the present invention may be made of low cost materials to reduce overall manufacturing cost and is easily sterilized during manufacture according to well-known techniques, if necessary. Preferably, the component layers and adhesives used to prepare the bandage are antistatic in character. This characteristic is preferred in order to pass the necessary tests needed to enable surgical use in accordance with the standards set by the National Fire Prevention Association, Bulletin No. 56A, dealing with the prevention of fires in operating rooms.

Other features and advantages of the invention will be apparent to those skilled in the art from the following detailed description of a preferred embodiment accompanied in the attached drawings.

Figure 1:
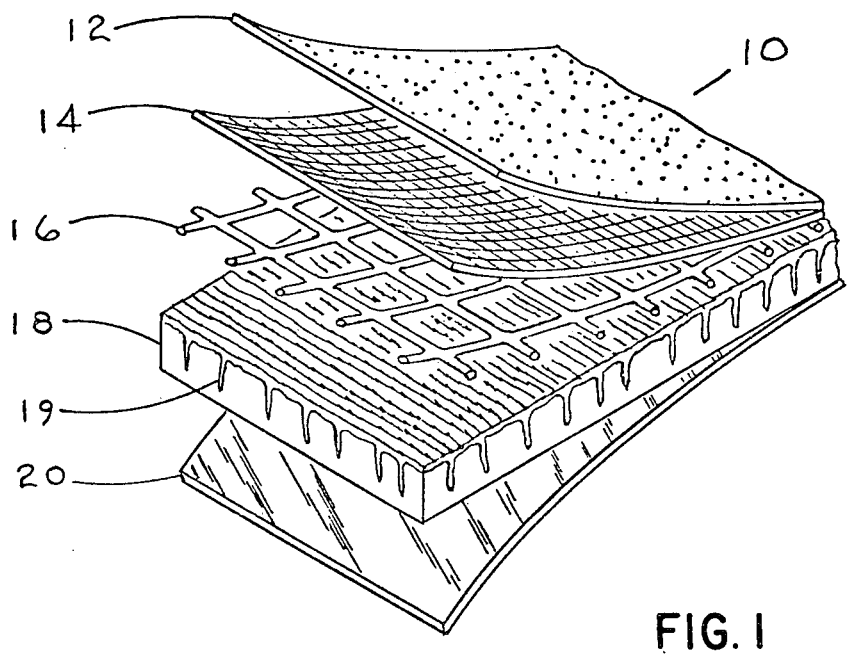
FIG. 1 is a perspective view of the various layers and components, in superimposed separated relation, illustrating the bandage of the present invention.

Referring to FIG. 1, reference numeral 10 designates the component layers of an absorbent bandage according to the present invention which contains five distinct layers. On one side is exterior layer 12 which is intended to be applied to the wound or incision. In any bandage being applied to a wound or incision, it is essential that no particles from the bandage come free and enter the wound. Accordingly, exterior layer 12 may be made from a multitude of materials which are capable of transmitting fluid between the wound and the bandage and which aids in preventing abrasion of the underlying absorbent materials. In addition, it may be used as an adherent material to enable selected removal of destroyed tissue and debris from the wound. Exterior layer 12 is preferably a perforated polyethylene film or a non-woven web material containing apertures.

When a top layer is selected which will not adhere to the wound it has been found preferable to use a perforated polyethylene film sold under the trademark DELNET, by Hercules Company of Wilmington, Del. It should be recognized, however, that other thermoplastic materials may be equally employed. Best results have been obtained using a polyethylene film having a thickness of about 1.0 mil with sufficient perforations to enable fluid transfer without escape of particulate matter from the bandage. Thicknesses larger and smaller than 1.0 mil may be employed provided adequate flexibility is achieved without the formation of a water barrier. This film is especially effective as an exterior layer to transmit fluid from the wound without absorbing fluid from the wound or bandage while maintaining the pad as an integral unit.

When exterior layer 12 is selected from a material designed to adhere to the wound, it has been found preferable to use a non-woven web material containing apertures such as the Chicopee Manufacturing Co. trademarked product, "KEYBACK," or the Burlington Industries trademarked product, "SPUNLACE." Such non-woven web materials are absorbent and are made by known methods. Acceptable results have been obtained with the porous adherent fiber fabric when the layer has a thickness of about 0.05 to 2 mm., and may range from 0.5 ounces to 3 ounces per square yard by weight. The exact thickness and number of apertures of the non-woven web may vary depending upon the exterior flexibility and resiliency desired to maintain the pad's absorbency while preventing escape of particulate matter from the bandage.

The exterior layer 12 is bonded on one side to an absorbent cellulosic layer 14 with a suitable waterproof adhesive in a manner which does not form a film over the absorbent cellulosic layer. This may be achieved by use of a conventional applicator roll which places the adhesive on the underside of exterior layer 12 at various intervals or spaces to assure uniform bonding of the exterior layer to the absorbent cellulosic layer 14. Since the adhesive used must be a waterproof adhesive, it is important that the amount used be restricted to the minimum amount necessary to hold the layers together in order not to restrict the transmission of fluid in the structure, which amounts are well within the skill of the ordinary artisan.

The absorbent cellulosic layer 14 is preferably selected from a material which has the ability to absorb fluid laterally and spread the fluid deposit rapidly outwardly from the point of impact. This layer may be formed from a plurality of sheets of highly absorbent, porous, fibrous, soft paper of the quality used in facial tissue. Such paper may be creped up to 50 percent according to conventional techniques. Other suitable, highly absorbent soft flexible material are non-woven, loosely spaced cellulosic materials. A preferable material is sold under the trademark, "HILOFT" by Scott Paper Company and more fully described in U.S. Pat. No. 3,879,257. This material is preferred since it absorbs approximately 10 times its weight in fluid while spreading the fluid laterally in all directions without clumping. In contrast, lesser amounts of absorption have been found when using the layers of tissue. Similar material is also available from the American Can Company under the trademark "BOLT" which may also be used. In order to avoid escape of particulate matter from the loosely bound cellulosic material, the surface fibers of this absorbent layer are preferably held in place by a fiber sealant such as polyvinyl acetate, polyamides and polyurethanes, printed in a grid pattern to allow for liquid penetration.

The third layer is grid material 16 to which may be a screen or open network of loosely-woven, spaced fibers formed into a generally orthogonal array or grid. The fibers or filaments of the grid material are preferably synthetic, such as nylon, polyolyfin or polyester. The grid is preferably a thin, soft layer composed of water resistant fibers in wide spaced relation so that the fibers facilitate conduction of fluid to the core absorbent material without itself absorbing the fluid. The grid may be interwoven, knit or joined together in any suitable manner to form apertures which must be large enough to pass fluid between absorbent layers 14 and 18. It has been found that fluid flow is hindered by use of nonsynthetic materials which have the tendency to hold water in small amounts and prevent fluid transfer. Grid material which has between 1 and 20 and preferably between 2 and 6 openings per inch has been found preferable to prepare a bandage which maintains its structural integrity and resists tearing when in use, while permitting a very high rate of fluid flow despite the resistance to wetting of the grid. While the exact mechanism of action of the grid material is not known, other than its function as a tear resistant structure, it is believed that the grid, once adhered between the two absorbent layers, provides a minimum amount of bonding surface necessary for holding the absorbent layers together and thus creates an air space narrow enough to create a capillary action enabling the rapid transmission of the laterally flowing fluid in the cellulosic material to the flexible absorbent member.

In the manufacture of the bandage, the grid material 16 is coated with a waterproof adhesive on both sides and then passed between the bottom of the cellulosic layer 14 and the top of the flexible absorbent member 18. By placing the adhesive directly on the grid material, the amount of adhesive used is restricted to the top and bottom of the filaments of the grid, and thus does not inhibit fluid flow.

The underside of grid material 16 is bonded to the core absorbent material identified in FIG. 1 as flexible absorbent member 18. The flexible absorbent member 18 is composed of synthetic cellular sponge material having numerous hydrophilic fiber bundles 19 extending from the surface of the sponge into the main body thereof without passing through the far side of the sponge material. By providing in the synthetic cellular sponge material numerous hydrophilic fibers extending from the surface inwardly, even though the sponge material may be hydrophobic, the fiber bundles or needles act to draw fluid from the surface of the sponge material into the cellular sponge material where it is deposited. Such structures are described in U.S. Pat. No. 3,156,242, which is incorporated herein by reference.

Any hydrophilic fibers my be used that can be placed in the cellular sponge sheet so as to extend from a surface of the sheet down into the sponge body. In using the term "hydrophilic fibers," those fibers or filaments, including continuous filaments, are included which have the natural property of moving aqueous fluids along their length by capillary action, either as a single fiber or fiber bundles, as well as those fibers and filaments which, although normally are not wetted by water, have been treated so as to make the same readily wettable so that they will move aqueous fluids along their surface. It is generally preferred to use cellulosic fibers, such as the natural cellulosic fibers including cotton, rayon, jute, hemp, and bagasse, and the synthetic cellulosic fibers, such as those formed of regenerated cellulose and cellulose acetate.

The preferred fibers used in forming the web are rayon fibers having a length of about ½ to 1½ inches. Longer fibers are not preferred since they become rigid and unyielding once needle-punched into the sponge material. Also the denier of the fibers should be about ½ to 3. Where the denier is too low, the fibers are difficult to handle and tend to break during the needling operation, whereas higher denier values tend to reduce the absorbency capacity of the sponge material.

Any cellular sponge material may be used such as hydrophobic sponge that is sufficiently flexible and resilient for the purpose intended. It is generally preferred to use sponges formed of polyurethane, polyesters, polyethers, nylon, polyethylene, rubber, polyvinyl chloride, and formalinized polyvinyl alcohol, or other materials which will remain resilient and flexible without the need of added plasticizers. However, the invention is not limited thereto, and plasticized sponges may be used in practicing the same. In general, the sponge should be readily flexible and conformed in a web of about ¼ to ¾ inch thickness and should be soft and resilient in nature. Thinner materials do not achieve an adequate fluid absorptive capacity whereas thicker materials are rigid and do not achieve adequate resiliency. The material should be sufficiently flexible and conforming to fit over body contours and be sufficiently soft and resilient to act as a protective cushion without irritation as occurs with a stiff sponge structure.

The underside of the flexible absorbent member 18, free of protruding fiber bundles is adhesively bound to a moisture resistant barrier layer 20. The moisture resistant layer retains any moisture held by the absorbent bandage to prevent wetting of clothes, bed coverings, and loss of fluid by evaporation into the atmosphere. The moisture resistant barrier may be derived from a wide variety of materials and is preferably a polyethylene film having a thickness of about 0.6 to about 1 mil, although thicker materials may be used since its function is solely to curtail fluid loss. It will be appreciated that other moisture-resistant barriers may likewise be employed.

The adhesives used to bond the respective layers together are well known in the bandage art. Exemplary adhesives that can be employed must be water resistant upon setting and curing. That result may be achieved by using heat and pressure sensitive adhesives as well as solvent based adhesives. Preferred adhesives include polyurethane adhesives, such as those described by Tranck, U.S. Pat. No. 3,769,071, incorporated by reference. The preferred polyurethane adhesives are those which are noncytotoxic and which are able to maintain their structural integrity, i.e. insolvency, in the presence of water. Also useable are acrylate esters such as isoamyl acrylate, the acrylate ester of commercial fusel oil, 2-ethyl butyl acrylate, ethyl acrylate, isooctyl acrylate and the like set forth in U.S. Pat. No. 2,925,174, also incorporated by reference herein.

Figure 2:
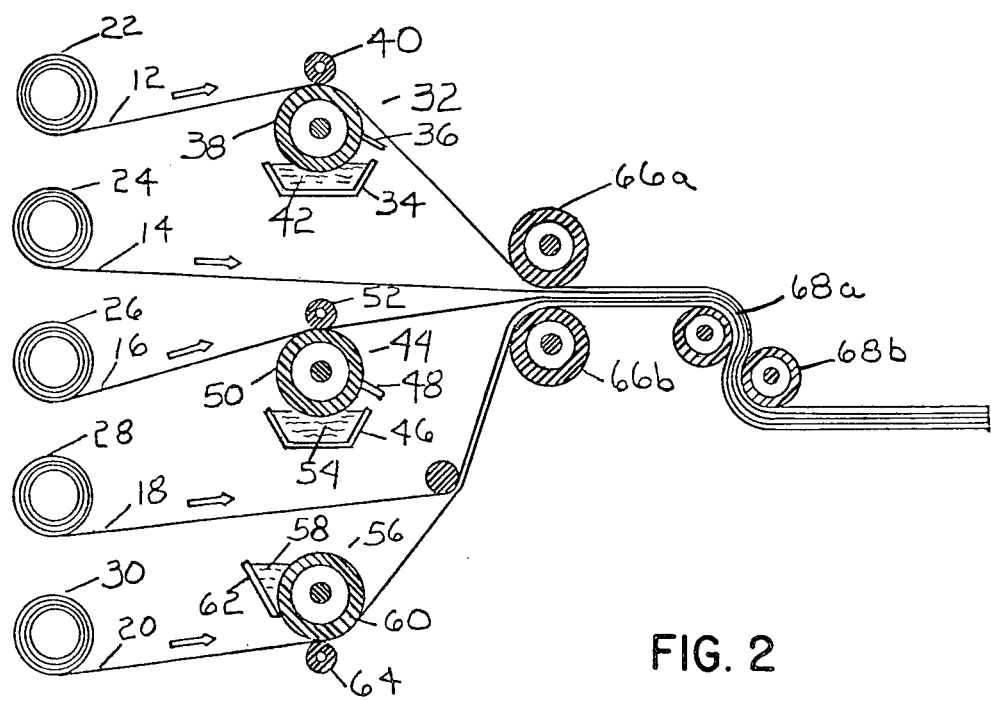
FIG. 2 is a schematic elevation view illustrating a process for making a laminate of the layers shown in FIG. 1.

FIG. 2 illustrates a process for producing the five-ply laminate structure 10 of FIG. 1, in accordance with the present invention. The layers 12, 14, 16, 18 and 20 forming the absorbent bandage 10 are unwound from separate supply rolls 22, 24, 26, 28 and 30, respectively.

Exterior layer 12 is guided to an adhesive application station 32 which includes a trough 34, doctor blade 36, an applicator roll 38, and a rubber impression roll 40. Roll 40 may be engraved on its surface so as to transfer a conventional adhesive composition 42 within trough 34 to the underside of exterior layer 12.

Grid material 16 is guided to an adhesive application station 44, which like station 32 includes a trough 46, doctor blade 48, an applicator roll 50 and a rubber impression roll 52. Roll 52 transfers a conventional adhesive composition 54 within trough 46 to both sides of grid material 16 using a single applicating surface on roll 50 in view of the void areas in the grid material 16.

Moisture resistant barrier layer 20 is guided to an adhesive application station 56. An adhesive composition 58 is supplied to the applicator roll 60 downstream from a doctor blade 62 from roll 64 to be transferred by roll 60 onto the inside surface of exterior barrier 20.

Impression rolls 66a, 66b, draw layers 12, 14, 16, 18 and 20 between rolls 66 while simultaneously pressing the adhesive coating on the inner surface of exterior layer 12 against the top surface of the absorbent cellulosic layer 14, the adhesive coating on the grid material 16 against the lower surface of the absorbent cellulosic layer 14 and top surface of the flexible absorbent member 18 with the grid material facing the fibers on the surface of the sponge material, and finally the adhesive coating on the inner surface of the barrier layer 20 against the lower surface of the absorbent member 18, notably the sponge material.

The five-layer highly absorbent laminate structure is then carried between hot rolls 68a, 68b to remove excess processing solution and to hasten the curing process of the adhesive. This may be achieved by applying conventional pressures under elevated temperatures to the laminate structure, such as at 12 to 60 pounds pressure per lineal inch at temperatures from about 180° to 300° F. While the process described above includes a unitary pressing scheme, it should be recognized that other conventional processes may be employed to prepare the laminated structure of this invention.

A pad thus formed has been found to provide a very rapid fluid absorption together with a high capacity for absorbing and holding fluid and medication which comes into contact with the wound incision as well as substantial retention of liquids to aid in treatment. The bandage provides a means for gently removing damaged tissue with each change of pad and in the alternative, can provide a surface which will not stick to the wound even after continuous contact for extended periods of time. The pad provides for substantial absorptive capacity to act as a reservoir of liquids and medication by creating a system whereby the initial flow of fluid is dispersed laterally by the underface cellulosic material, and then dispersed vertically through the sponge material, to be again absorbed laterally from the roots of needle-punched fiber bundles.

The bandage is applied to the victim in cases of severe burn wounds by wrapping the victim either partially or completely in a pad containing the requisite water and optimal fluid. Once placed around the victim, additional attachments such as tape may be used to prevent it from sliding off the wound if necessary. Such means may also be physically attached to the end of the bandage in the form of pressure-sensitive adhesives or other conventional joining means.

The following examples are given to further illustrate the invention. All percentages given are based upon weight unless otherwise indicated.

INVENTIVE EXAMPLE 1

A web of carded rayon fibers having a denier of about ½ and a fiber length of about 1½ inches was placed on top of a polyurethane foam and needle punched into the polyurethane foam with a needling machine. The needles are made to penetrate the sponge material and web from the surface containing the web drawing the fibers down into the sponge without passing the fibers through the other side of the sponge. This composite is flexible, resilient and highly absorbent. This absorbent material was then simultaneously brought into contact with four additional layers, notably, an exterior layer, an absorbent cellulosic layer, a grid material and moisture resistant barrier, and pressure rolled into a composite laminate structure. Adhesion was achieved by depositing on the inner surfaces of the exterior layer and moisture resistant barrier an adhesive by means of an engraved applicator roll, said engraving being in the form of a regular diamond cellular pattern having approximately 120 quads (cells) per lineal inch. The adhesive was a polyurethane waterproof adhesive sold by National Starch and Chemical Co., Product No. 9125 to enable efficient coating of the layers. The exterior layer was made from "DELNET" manufactured by Hercules, Incorporated. The moisture resistant barrier was a waterproof polyethylene film manufactured by Oxford Division of The Hartford Corporation. Adhesive was applied to the grid material which had 4 openings per inch by passing the grid over a roll coated with the above adhesive, which because of the voids in the grid, coated the entire surface of the grid. The loosely woven absorbent cellulosic material had a polyvinyl acetate surface coating and was identified as "HI-LOFT" manufactured by Scott Paper Company.

Once the adhesive was applied to the layers contacted, all of the layers were passed through a roll mill and pressed together under a pressure of about 40 pounds per lineal inch and then heat cured to remove the adhesive solvent at a temperature of about 250° F. at 40 pounds per lineal inch pressure. Following heat treatment, the laminate structure was cooled to room temperature and tested for water absorbency.

The water absorbency test was performed according to the American Association of Textile Chemists and Colorists (AATCC) test publication 42-1977. In this manner, a 6×18 inch piece of test material is mounted on an inclined plane at a 12° angle. Directly above a center line and 1½ inch from the highest point, a funnel with a spray nozzle is placed with its bottom being 4 inches above the material. 100 cc. of water is then poured into the funnel which sprays on the material. The weight of the material both before and after water treatment is compared. The inventive structure tested resulted in the absorption of 86 cc. of water.

COMPARATIVE EXAMPLE A AND B

The procedure of Example 1 was employed to prepare comparative structures A and B. In comparative A, no grid material was employed and in comparative B the absorbent cellulosic material was switched with the needle-punched rayon sponge material.

When the water absorbency test of Example 1 was repeated, comparative structure A without the grid material showed a water retention of 37 cc. and comparative structure B showed a water retention of about 40 cc. The results from comparative structure A indicate the essential presence of the grid material to separate the two critical absorbent layers to achieve high water absorption. In contrast, comparative structure B was unacceptable for a bandage structure. Once the structure was wetted, short needle-like filaments of the rayon web located on top of the sponge material began passing through the open weave of the exterior layer. This exposure of particulate matter would enter open wounds causing granulitis upon use rendering the structure completely useable.

COMPARATIVE EXAMPLE C

In this Example, a commercially available structure was tested for its water absorptive capacity. The structure consisted of approximately 30 layers of tissue paper within a facing of laminated gauze and non-woven nylon fabric having a backing of polyethylene film. The structure was sealed around the parameter. A 4×4 inch sample of this comparative structure was weighed, immersed in water and reweighed to determine its absorptive capacity. The structure showed a water retention of 18.62 grams. When this test was repeated with the inventive structure of Example 1, the inventive structure retained 37.81 grams of water, which amount is over twice as much water as the comparative material. The absorptive capacity of the inventive structure equates to approximately 3.75 liters of water per square meter, which amount of absorption is extremely high.

The invention being thus described, it will be obvious that the same may be varied in many ways. Such variations are not to be regarded as a departure from the spirit and scope of the invention and all such modifications are intended to be included within the scope of the following claims.

What is claimed is:

1. A multilayer absorbent structure, which comprises:
   (a) an exterior layer which contacts the wound surface;
   (b) an absorbent cellulosic layer joined to the exterior layer;
   (c) a nonabsorbent grid material which is joined on one side to the absorbent cellulosic layer and on the other side to a flexible absorbent member;
   (d) said flexible absorbent member formed of a flexible sheet of sponge material containing a web of absorbent fibers disposed on the flexible sheet and extending into the flexible sheet without extending through the flexible sheet;
   (e) a moisture resistant barrier layer making an outer layer which is joined to the lower side of the sponge material portion of the flexible absorbent member.

2. The absorbent structure of claim 1 wherein the exterior layer is a porous non-woven web material.

3. The absorbent structure of claim 1 wherein the exterior layer is a perforated thermoplastic material.

4. The absorbent structure of claim 1 wherein the absorbent cellulosic layer is composed of a plurality of sheets of absorbent, porous, fibrous tissue.

5. The absorbent structure of claim 1 wherein the absorbent cellulosic layer is a non-woven, loosely spaced cellulosic material.

6. The absorbent structure of claim 1, wherein the grid material has apertures between 1 and 20 openings per inch.

7. The absorbent structure of claim 1 wherein an adhesive is applied to the grid material for bonding together the absorbent cellulosic layer and the flexible absorbent member.

8. The absorbent structure of claim 1 wherein the flexible absorbent structure contains a web of rayon needle-punched into the sponge material.

9. The absorbent structure of claim 8 wherein the sponge structure is a polyurethane foam having a thickness of about ¼ to ¾ inch.

10. The absorbent structure of claim 1 wherein the moisture resistant barrier layer is a film of polyethylene.

11. A multilayer absorbent structure, which comprises:
 (a) an exterior layer which contacts the wound surface selected from a porous non-woven web material or a perforated thermoplastic material;
 (b) a non-woven, loosely spaced absorbent cellulosic layer joined to the exterior layer;
 (c) a nonabsorbent grid material having between 1 and 20 openings per inch and which is joined on one side to the absorbent cellulosic layers and on the other side to a flexible absorbent member;
 (d) said flexible absorbent member formed of a flexible sheet of polyurethane foam containing a web of rayon fibers disposed on the foam and extending into but not through the foam; and
 (e) a moisture resistant barrier layer making an outer layer which is joined to the lower side of the sponge material portion of the flexible absorbent member.

12. A process for preparing a multilayer absorbent structure which comprises:
 (a) bonding two absorbent layers to a grid material having between 1 and 20 openings per inch so that the grid material separates the two absorbent layers, said absorbent layers comprising an absorbent cellulosic layer and a flexible absorbent material formed of a flexible sheet of sponge material covered with a web of needle pressed absorbent fibers;
 (b) bonding an exterior layer which is capable of transmitting fluid to the absorbent cellulosic layer; and
 (c) bonding a moisture resistant barrier to the sponge material of the flexible absorbent material.

13. The process of claim 12 wherein bonding is achieved by applying an adhesive to the exterior layer and moisture resistant barrier layer in given pattern so that when these layers are bonded to the exterior surfaces of the absorbent layers only a portion of the surface of the absorbent layers is bonded, thereby leaving a sufficient amount of area available for fluid transfer.

14. The process of claim 12 wherein an adhesive is applied to the grid material by passing the grid material over an adhesive coated roll which because of the voids in the grid, coats the entire surface of the grid material.

15. The process of claim 12 wherein the five layers are pressed together in a single step.

16. The process of claim 15 wherein pressing is achieved at 12 to 60 pounds pressure per lineal inch and at temperatures from about 180° to 300° F.

* * * * *